United States Patent [19]
Kimura et al.

[11] Patent Number: 5,723,141
[45] Date of Patent: Mar. 3, 1998

[54] N-PYRIDYLTOLUIDINE-CONTAINING FUNGICIDAL WATER DISPERSIBLE GRANULES

[75] Inventors: Tokiya Kimura; Takeshi Shindo; Kazutaka Ikeda, all of Kusatsu, Japan

[73] Assignee: Ishihara Sangyo Kaisha Ltd., Osaka, Japan

[21] Appl. No.: 592,296

[22] PCT Filed: Aug. 10, 1994

[86] PCT No.: PCT/JP94/01320

§ 371 Date: Feb. 9, 1996

§ 102(e) Date: Feb. 9, 1996

[87] PCT Pub. No.: WO95/04460

PCT Pub. Date: Feb. 16, 1995

[30] Foreign Application Priority Data

Aug. 11, 1993 [JP] Japan .................................. 5-220563

[51] Int. Cl.$^6$ ...................................................... A01N 25/12

[52] U.S. Cl. ...................... 424/408; 424/409; 424/417; 424/421; 514/352

[58] Field of Search ........................ 424/405, 408, 424/409, 417–422; 514/352

[56] References Cited

FOREIGN PATENT DOCUMENTS

| | | |
|---|---|---|
| 59027804 | 2/1984 | Japan . |
| 60197606 | 10/1985 | Japan . |
| 62000403 | 1/1987 | Japan . |
| 2160703 | 6/1990 | Japan . |
| 2174706 | 7/1990 | Japan . |

*Primary Examiner*—Neil S. Levy
*Attorney, Agent, or Firm*—Oblon, Spivak, McClelland, Maier & Neustadt, P.C.

[57] ABSTRACT

N-pyridyltoluidine-containing fungicidal water dispersible granule which comprises 3-chloro-N-(3-chloro-5-trifluoromethyl-2-pyridyl)-α,α,α-trifluoro-2,6-dinitro-p-toluidine as a fungicidal active component, a surfactant and a carrier, and of which a 1% water suspension is acescent.

10 Claims, No Drawings

N-PYRIDYLTOLUIDINE-CONTAINING FUNGICIDAL WATER DISPERSIBLE GRANULES

TECHNICAL FIELD

The present invention relates to a pesticidal composition containing 3-chloro-N-(3-chloro-5-trifluoromethyl-2-pyridyl)-α,α,α-trifluoro-2,6-dinitro-p-toluidine (hereinafter referred to as fluazinam) as the fungicidal active component. More particularly, it relates to N-pyridyltoluidine-containing fungicidal water dispersible granules having the color change suppressed without reducing dispersibility and suspensibility in water.

BACKGROUND ART

Fluazinam is an active ingredient of an agricultural or horticultural fungicide, and a wettable powder or a suspension concentrate may, for example, be mentioned as its formulation to be diluted with water and sprayed.

Generally, a powder formulation such as a wettable powder has a problem of dusting at the time of weighing or preparation into an application form, and a liquid formulation such as a suspension concentrate has a problem in the treatment of a polluted bottle after use. As one of the disposal to solve such problems, an attempt has been made in recent years to granulate the wettable powder.

However, when it is attempted to granulate a wettable powder containing fluazinam, there have been problems such that the dispersibility and suspensibility in water decreases, and the product undergoes a color change. If the dispersibility or suspensibility in water decreases, uniform application tends to be difficult, and a spray nozzle is likely to be clogged. Consequently, the fungicidal activity tends to be low or no-uniform, such being undesirable. With the one which undergoes a substantial color change with time, there may be some chemical change in the fungicidal active component or its adjuvants, and some times its commercial value tends to be low. Therefore, such a product may sometimes be hardly acceptable as a pesticidal commercial product.

DISCLOSURE OF INVENTION

It is an object of the present invention to provide N-pyridyltoluidine-containing fungicidal water dispersible granules, as a pesticidal composition containing fluazinam as an active ingredient, which has the color change suppressed without reducing the dispersibility and suspensibility in water.

The present inventors have prepared N-pyridyltoluidine-containing fungicidal water dispersible granules containing various components and examined dispersibility and suspensibility in water after durability tests and as a result, they have unexpectedly found that there is a certain relation between the acidity of the water dispersible granules and the dispersibility and suspensibility in water. Further, it has been found that the color change of the product can be suppressed by adjusting N-pyridyltoluidine-containing fungicidal water dispersible granules so that when they are suspended in water, they have acescence. The present invention has been accomplished on the basis of these discoveries.

Thus, the present invention provides N-pyridyltoluidine-containing fungicidal water dispersible granules, which comprises fluazinam as a fungicidal active component, a surfactant and a carrier, and of which a 1% water suspension is acescent, that is slightly acidic.

The fungicidal active component of the above water dispersible granules may contain fluazinam alone, or may contain in addition to fluazinam, another fungicidal active ingredient which does not adversely affect the dispersibility and suspensibility in water. Such another fungicidal active ingredient may, for example, be 1-(2-cyano-2-methoxyiminoacetyl)-3-ethylurea (hereinafter referred to as cymoxanil), tetrachloroisophthalonitrile (hereinafter referred to as chlorothalonil), dimethyl 4,4'-(o-phenylene) bis(3-thioallophanate) (hereinafter referred to as thiophanate-methyl), 4-[3-(4-chlorophenyl)-3-(3,4-dimethoxyphenyl)acryloyl]morpholine (hereinafter referred to as dimethomorph), (RS)-3-(3,5-dichlorophenyl)-5-methyl-5-vinyl-1,3-oxazolidine-2,4-dione (hereinafter referred to as vinclozolin), 3-(3,5-dichlorophenyl)-N-isopropyl-2,4-dioxoimidazolidine-1-carboxamide (hereinafter referred to as iprodione), N-(3,5-dichlorophenyl)-1,2-dimethylcyclopropane-1,2-dicarboximide (hereinafter referred to as procymidone), 3'-isopropoxy-o-toluanilide (hereinafter referred to as mepronil), α,α,α-trifluoro-3'-isopropoxy-o-toluanilide (hereinafter referred to as flutolanil), methyl (E)-methoxyimino-[α-(o-tolyloxy)-o-tolyl]acetate, methyl (E)-2-{2-[6-(2-cyanophenoxy)pyrimidin-4-yloxy]phenyl}-3-methoxyacrylate, (E)-2-methoxyimino-N-methyl-2-(2-phenoxyphenyl)acetamide, N-(4,6-dimethylpyrimidin-2-yl) aniline (hereinafter referred to as pyrimethanil) or 2-anilino-4-methyl-6-(1-propynyl)pyrimidine (hereinafter referred to as mepanipyrim). Among them, cymoxanil, chlorothalonil, thiophanate-methyl or dimethomorph is preferred.

The N-pyridyltoluidine-containing fungicidal water dispersible granules of the present invention include (1) those containing fluazinam alone as the fungicidal active component, and (2) those containing fluazinam and another fungicidal active ingredient, as the fungicidal active component.

As the above surfactant, various types may be employed, but anionic or nonionic surfactants may be mainly employed.

As the surfactant useful for N-pyridyltoluidine-containing fungicidal water dispersible granules of the present invention, the following examples will be given, but the useful surfactant is not limited to such specific examples.

Anionic surfactants $C_{12}$–$C_{18}$ alkylsulfonate $C_8$–$C_{12}$ alkylphenylsulfonate Mono- or di-$C_8$–$C_{12}$ alkylnaphthalenesulfonate Polyoxyethylene $C_{12}$–$C_{18}$ alkyl ether sulfate Polyoxyethylene $C_8$–$C_{12}$ alkylphenyl ether sulfate Polyoxyethylene polyoxypropylene block-polymer sulfate Polyoxyethylene mono-, di- or tri-styryl phenyl ether sulfate Polyoxyethylene $C_{12}$–$C_{18}$ alkyl ether phosphate Polyoxyethylene $C_8$–$C_{12}$ alkylphenyl ether phosphate Polyoxyethylene mono-, di or tri-styryl phenyl ether phosphate Di- $C_6$–$C_8$ alkylsulfosuccinate Naphthalene sulfonate, formaldehyde condensate Mono- or di- $C_1$–$C_4$ alkylnaphthalene sulfonate, formaldehyde condensate Lignin sulfonate Salt of polyacrylic acid Alkali metal salt of copolymer-having carboxyl groups.

The above anionic surfactants can be used in the form of salts or acids. As the salts, alkali metal salts such as sodium or potassium salts, alkaline earth metal salts such as calcium salts, ammonium salts, or amine salts may be mentioned.

Nonionic surfactants

Polyoxyethylene $C_{12}$–$C_{18}$ alkyl ether

Polyoxyethylene $C_8$–$C_{12}$ alkylphenyl ether

Polyoxyether mono-, di- or tri-styryl phenyl ether

Polyoxyethylene sorbitan fatty acid ester

Polyoxyethylene $C_{12}$–$C_{18}$ fatty acid ester

Poly(vinylpyrrolidone)

Poly(vinyl alcohol)

Carboxymethyl cellulose

Further, the water dispersible granules of the present invention are prepared into a composition so that its 1% water suspension will be acescent. Even a cationic or amphoteric surfactant may be employed so long as it meets the above mentioned conditions, and it does not impair the function.

As the above mentioned carrier, mineral powder or water-soluble powder may, for example, be employed.

As the mineral powder, diatomaceous earth, talc, clay, bentonite, silica or alumina may, for example, be mentioned. As the water-soluble powder, saccharides such as milk sugar, fruit sugar or grape sugar, or a salt, for example, an alkali metal salt or ammonium salt of a mineral acid such as hydrochloric acid or nitric acid, an alkali metal salt, partial alkali metal salt, ammonium salt or partial ammonium salt of a mineral acid such as sulfuric acid, phosphoric acid or boric acid. Here, the partial alkali metal salt or the partial ammonium salt may, for example, be sodium hydrogensulfate, sodium monohydrogenphosphate, sodium dihydrogenphosphate or ammonium hydrogensulfate.

Suitable blend proportions of the above respective components can not generally be defined, because they may differ depending upon the types of the blend components and the blending methods. However, usually, the fungicidal active component is from 20 to 94 wt %, the surfactant is from 2 to 30 wt %, and the carrier is from 1 to 78 wt %.

The water dispersible granules of the present invention are a composition prepared so that its 1% water suspension (a suspension of the water dispersible granules in distilled water) will have acescence. The acescence is preferably from pH 5.0 to pH 6.8. If the pH of the above 1% water suspension is less than 5.0, the dispersibility and suspensibility in water tend to deteriorate, although no color change will be observed. On the other hand, if the pH exceeds 6.8, the color change tends to be observed, although no deterioration of dispersibility and suspensibility may be observed.

In a case where the 1% water suspension will not be acescent even when the above fungicidal active component, the surfactant and the carrier are mixed, a pH control agent may separately be added to attain the desired acescence.

As such a pH control agent, an organic carboxylic acid such as acetic acid, propionic acid, citric acid, malonic acid, maleic acid, fumaric acid, succinic acid, malic acid or tartaric acid, or a non-volatile mineral acid such as sulfuric acid, phosphoric acid or boric acid, may be employed.

The proportion of the pH control agent to be additionally incorporated, is from 0 to 3 wt % in the water dispersible granules.

Thus, the desired acescence of the 1% water suspension can be accomplished by using, for example, one or more of acidic anion surfactants as the surfactant, one or more of acidic mineral powders or an acidic water-soluble powder as the carrier or pH control agents.

When the fungicidal active component is subjected to wet-milling for the preparation of the water dispersible granules of the present invention, an antifoamer such as dimethyl polysiloxane may be incorporated.

The water dispersible granules of the present invention can be produced by a conventional method such as extruding granulation, spray drying granulation, fluidized bed granulation, tumbling granulation or agitation granulation. However, it is preferred to produce them by extruding granulation, spray drying granulation or fluidized bed granulation.

In the extruding granulation, for example, from 80 to 95 parts by weight of fluazinam and a small amount of a carrier are mixed and pulverized to obtain a pulverized mixture, or from 20 to 80 parts by weight of fluazinam, from 1 to 10 parts by weight of a surfactant, from 0 to 0.2 parts by weight of an antifoamer and from 19 to 79 parts by weight of water are mixed and then wet-milled to obtain a slurry. To this pulverized mixture or slurry, a surfactant and a carrier, and, if necessary, a pH control agent are added. The mixture is mixed, water is added thereto, and the mixture is kneaded and then granulate by an extruder, followed by drying. Here, the amounts of the respective components are such that fluazinam is from 20 to 94 wt %, the surfactant is from 2 to 30 wt %, the pH control agent is at most 3 wt %, the antifoamer is at most 0.2 wt % and the carrier is from 1 to 78 wt %. Otherwise, to the above pulverized mixture or to the above slurry, another fungicidal active ingredient and the above specified amounts of the surfactant, the carrier and, if necessary, the pH control agent, are mixed, and water is added thereto. The mixture is kneaded and then granulated by an extruder, followed by drying. Said another fungicidal active ingredient may be mixed and pulverized with fluazinam to obtain said pulverized mixture, or wet-milled with fluazinam to obtain said slurry. Here, the total amount of fluazinam and another fungicidal active ingredient is from 20 to 94 wt %, based on the entire composition.

In the spray drying granulation or the fluidized bed granulation, for example, from 20 to 80 parts by weight of fluazinam, from 1 to 10 parts by weight of a surfactant, from 0 to 0.2 parts by weight of an antifoamer and from 19 to 79 parts by weight of water are mixed and then wet-milled to obtain a slurry. To this slurry, a carrier and, if necessary, a surfactant, a pH control agent and water are added, followed by mixing. The mixture is granulated by a spray dryer or a fluidized bed granulating machine, or by an apparatus having the two unified (such as a fluidized bed spray dryer), followed by drying. Here, the amounts of the respective components are such that fluazinam is from 20 to 94 wt %, the surfactant is from 2 to 30 wt %, the pH control agent is at most 3 wt %, the antifoamer is at 0.2 wt %, and the carrier is from 1 to 78 wt %. Otherwise, from 10 to 70 parts by weight of fluazinam, from 10 to 70 pars by weight of another fungicidal active ingredient, from 1 to 10 parts by weight of the surfactant, from 0 to 0.2 parts by weight of the antifoamer and from 19 to 79 parts by weight of water are mixed and then wet-milled to obtain a slurry. To the slurry, the carrier and, if necessary, a surfactant, a pH control agent and water are added, followed by mixing. The mixture may be granulated by a spray dryer or a fluidized bed granulating machine, or by an apparatus having the two unified (such as fluidized bed spray dryer), followed by drying. Said another fungicidal active ingredient may be added after the wet-milling. Here, the total amount of fluazinam and another fungicidal active ingredient is from 20 to 94 wt % based on the entire composition.

Now, the present invention will be described in further detail with reference to Examples. However, it should be understood that the present invention is by no means restricted to such specific Examples.

EXAMPLE 1

96 parts by weight of fluazinam and 4 parts by weight of fine silica were pulverized by a jet mill. 85 parts by weight of this pulverized mixture was mixed with the following components (1) to (5):

(1) Polyoxyethylenetristyrylphenyl ether sulfate (Soprophor 4D384, manufactured by Rhône-Poulenc) . . . 2 parts by weight (2) Sodium salt of methylnaphthalenesulfonate, formaldehyde condensate (Supragil MNS/90, manufactured by Rhöne-Poulenc) . . . 4 parts by weight (3) Mixture of sodium salt of a copolymer having carboxyl groups and polyoxyethylenedistyrylphenyl ether sulfate (Geropon SC211, manufactured by Rhöne-Poulenc) . . . 4 parts by weight (4) Sodium sulfate . . . 4.5 parts by weight (5) Citric acid . . . 0.5 part by weight Then, water was added thereto, and the mixture was kneaded and granulated by an extruder (Screen: 0.8 mm in diameter) followed by drying to obtain a water dispersible granules.

EXAMPLE 2

96 parts by weight of fluazinam and 4 parts by weight of fine silica were pulverized by a jet mill. 85 parts by weight of this pulverized mixture was mixed with the following components (1) to (4):

(1) Polyoxyethylenetristyrylphenyl ether phosphate (Soprophor 3D33, manufactured by Rhöne-Poulenc) . . . 2 parts by weight (2) Sodium salt of methylnaphthalene sulfonate, formaldehyde condensate (Supragil MNS/90, manufactured by Rhöne-Poulenc) . . . 4 parts by weight (3) Mixture of sodium salt of a copolymer having carboxyl groups and polyoxyethylene distyryl phenylether sulfate (Geropon SC211, manufactured by Rhöne-Poulenc) . . . 4 parts by weight (4) Sodium dihydrogenphosphate dihydrate . . . 5 parts by weight Then, water was added thereto, and the mixture was kneaded and granulated by an extruder (Screen: 0.8 mm in diameter), followed by drying to obtain a water dispersible granules.

EXAMPLE 3

(1) Fluazinam . . . 72 parts by weight (2) Polyoxyethylenetristyrylphenyl ether sulfate (Soprophor 4D384, manufactured by Rhöne-Poulenc) . . . 1.5 parts by weight (3) Dimethyl polysiloxane . . . 0.1 part by weight (4) Water . . . 26.4 parts by weight The above components (1) to (4) were mixed and pulverized by a beads mill to obtain a slurry. Then, 85 parts by weight of this slurry was mixed with the following components (5) to (8):

(5) Sodium salt of methylnaphthalene sulfonate, formaldehyde condensate (Supragil MNS/90, manufactured by Rhöne-Poulenc) . . . 6 parts by weight (6) Sodium salt of a copolymer having carboxyl groups (Geropon T/36, manufactured by Rhöne-Poulenc) . . . 3 parts by weight (7) Sodium dihydrogenphosphate dihydrate . . . 10 parts by weight (8) Sodium sulfate . . . 5 parts by weight Then, water was added thereto, and the mixture was kneaded and granulated by an extruder (Screen: 0.8 mm in diameter), followed by drying to obtain a water dispersible granules.

EXAMPLE 4

96 parts by weight of fluazinam and 4 parts by weight of fine silica were pulverized by a jet mill. 63 parts by weight of this pulverized mixture was mixed with the following components (1) to (5):

(1) Cymoxanil . . . 19 parts by weight (2) Polyoxyethylene tristyryl phenyl ether sulfate (Soprophor 4D384, manufactured by Rhöne-Poulenc) . . . 2 parts by weight (3) Sodium salt of methylnaphthalene sulfonate, formaldehyde condensate (Supragil MNS/90, manufactured by Rhöne-Poulenc) . . . 4 parts by weight (4) Mixture of sodium salt of a copolymer having carboxyl groups and polyoxyethylene distyryl phenylether sulfate (Geropon SC211, manufactured by Rhöne-Poulenc) . . . 2 parts by weight (5) Sodium dihydrogenphosphate dihydrate . . . 8 parts by weight Then, water was added thereto, and the mixture was kneaded and granulated by an extruder (Screen: 0.8 mm in diameter), followed by drying to obtain a water dispersible granules.

EXAMPLE 5

96 parts by weight of fluazinam and 4 parts by weight of fine silica were pulverized by a jet mill. 30 parts by weight of this pulverized mixture was mixed with the following components (1) to (6):

(1) Thiophanate-methyl . . . 50 parts by weight (2) Polyoxyethylenetristyrylphenyl ether sulfate (Soprophor 4D384, manufactured by Rhöne-Poulenc) . . . 2 parts by weight (3) Sodium salt of methylnaphthalene sulfonate-formaldehyde condensate (Supragil MNS/90, manufactured by Rhöne-Poulenc) . . . 4 parts by weight (4) Mixture of sodium salt of a copolymer having carboxyl groups and polyoxyethylene distyryl phenylether sulfate (Geropon SC211, manufactured by Rhöne-Poulenc) . . . 4 parts by weight (5) Potassium dihydrogenphosphate . . . 4 parts by weight (6) Sodium sulfate . . . 6 parts by weight Then, water was added thereto, and the mixture was kneaded and granulated by an extruder (Screen: 0.8 mm in diameter), followed by drying to obtain a water dispersible granules.

EXAMPLE 6

96 parts by weight of fluazinam and 4 parts by weight of fine silica were pulverized by a jet mill. 40 parts by weight of this pulverized mixture was mixed with the following components (1) to (6):

(1) Dimethomorph . . . 40 parts by weight (2) Polyoxyethylenetristyrylphenyl ether sulfate (Soprophor 4D384, manufactured by Rhöne-Poulenc) . . . 2 parts by weight (3) Sodium salt of methylnaphthalene sulfonate-formaldehyde condensate (Supragil MNS/90, manufactured by Rhöne-Poulenc) . . . 4 parts by weight (4) Mixture of sodium salt of a copolymer having carboxyl groups and polyoxyethylenedistyrylphenyl ether sulfate (Geropon SC211, manufactured by Rhöne-Poulenc) ... 4 parts by weight (5) Potassium dihydrogenphosphate ... 5.4 parts by weight (6) Sodium sulfate ... 4.6 parts by weight Then, water was added thereto, and the mixture was kneaded and granulated by an extruder (Screen: 0.8 mm in diameter), followed by drying to obtain a water dispersible granules.

EXAMPLE 7

(1) Fluazinam ... 60 parts by weight (2) Polyoxyethylenetristyrylphenyl ether sulfate (Soprophor 4D384, manufactured by Rhöne-Poulenc) ... 1.5 parts by weight (3) Dimethyl polysiloxane ... 0.1 part by weight (4) Water ... 38.4 parts by weight The above components (1) to (4) were mixed and pulverized by a beads mill to obtain a slurry. Then, 67 parts by weight of this slurry was mixed with the following components (5) to (8):

(5) Sodium salt of methylnaphthalene sulfonate, formaldehyde condensate (Supragil MNS/90, manufactured by Rhöne-Poulenc) ... 3.5 parts by weight (6) Sodium salt of a copolymer having carboxyl groups (Geropon T/36, manufactured by Rhone-Poulenc) ... 1.5 parts by weight (7) Sodium dihydrogenphosphate dihydrate ... 3.8 parts by weight (8) Water ... 24.2 parts by weight Then, the mixture was granulated by a fluidized bed spray dryer, followed by drying to obtain a water dispersible granules.

With respect to the respective formulated products, the dispersibility and suspensibility in water and the color change before and after the durability test were examined.

The durability test was carried out by putting the respective formulated products in glass bottles, which were sealed and kept in a constant temperature oven at 54° C. for 2 weeks.

pH: 1 g of the formulated product was dispersed in 100 ml of distilled water, and then the pH was measured by a glass electrode pH meter.

Dispersibility in water: Into a 100 ml cylinder, 100 ml of standard water (Official Testing Methods of Japan for Agricultural Chemicals: Standard hard water which includes 53.6 ppm for converting $Na^+$ and $K^+$ to concentration of $CaCO_3$) was introduced, and 0.5 g of the formulated product was added thereto. One minute later, the cylinder was inverted, and the number of times (X) of such inversion until the granules are disintegrated, was counted.

Suspensibility in water: Into a 100 ml cylinder, 100 ml of the above mentioned standard water was introduced, and 0.5 g of the formulated product was added thereto. One minute later, the cylinder was inverted 30 times in one minute. The suspension thereby obtained was transferred to a 100 ml graduated cone shaped centrifuge tube and left to stand still for 15 minutes, whereupon the sediment volume (Y ml) was measured.

Color: Visually evaluated.

The results are shown in Table 1.

TABLE 1

|  | Before the durability test | | | | After the durability test | | |
| --- | --- | --- | --- | --- | --- | --- | --- |
|  | pH | Dispersibility in water (X) | Suspensibility in water (Y) | Color | Dispersibility in water (X) | Suspensibility in water (Y) | Color |
| Example 1 | 6.2 | 3 | less than 0.05 | Pale reddish yellow | 4 | 0.1 | No change |
| Example 2 | 6.3 | 5 | 0.05 | Pale yellow | 5 | less than 0.05 | No change |
| Example 3 | 5.8 | 6 | less than 0.05 | Pale yellow | 5 | less than 0.05 | No change |
| Example 4 | 6.2 | 4 | less than 0.05 | Pale yellow | 4 | less than 0.05 | No change |
| Example 5 | 6.4 | 5 | less than 0.05 | Pale yellow | 4 | less than 0.05 | No change |
| Example 6 | 6.1 | 6 | 0.1 | Pale yellow | 6 | 0.1 | No change |
| Example 7 | 6.4 | 2 | less than 0.05 | Pale yellow | 5 | less than 0.05 | No change |
| Comparative Example 1 | 7.3 | 4 | less than 0.05 | Pale yellowish brown | 4 | less than 0.05 | Changed to dark yellowish brown |
| Comparative Example 2 | 4.4 | 4 | less than 0.05 | Pale yellow | Not dispersed | Not dispersed | No change |

COMPARATIVE EXAMPLE 1

96 parts by weight of fluazinam and 4 parts by weight of fine silica were pulverized by a jet mill. 85 parts by weight of this pulverized mixture was mixed with the following components (1) to (4):

(1) Polyoxyethylenetristyrylphenyl ether sulfate (Soprophor 4D384, manufactured by Rhone-Poulenc) ... 2 parts by weight (2) Sodium salt of methylnaphthalene sulfonate, formaldehyde condensate (Supragil MNS/90, manufactured by Rhöne-Poulenc) ... 4 parts by weight (3) Mixture of sodium salt of a copolymer having carboxyl groups and polyoxyethylenedistyrylphenyl ether sulfate (Geropon SC211, manufactured by Rhône-Poulenc) . . . 4 parts by weight (4) Sodium sulfate . . . 5 parts by weight Then, water was added thereto, and the mixture was kneaded and granulated by an extruder (Screen: 0.8 mm in diameter), followed by drying to obtain a water dispersible granules.

COMPARATIVE EXAMPLE 2

96 parts by weight of fluazinam and 4 parts by weight of fine silica were pulverized by a jet mill. 85 parts by weight of this pulverized mixture was mixed with the following components (1) to (5):

(1) Polyoxyethylenetristyrylphenyl ether sulfate (Soprophor 4D384, manufactured by Rhône-Poulenc) . . . 2 parts by weight (2) Sodium salt of methylnaphthalene sulfonate-formaldehyde condensate (Supragil MNS/90, manufactured by Rhône-Poulenc) . . . 4 parts by weight (3) Mixture of sodium salt of a copolymer having carboxyl groups and polyoxyethylenedistyrylphenyl ether sulfate (Geropon SC211, manufactured by Rhône-Poulenc) . . . 4 parts by weight (4) Sodium sulfate . . . 3 parts by weight (5) Citric acid . . . 2 parts by weight Then, water was added thereto, and the mixture was kneaded and granulated by an extruder (Screen: 0.8 mm in diameter), followed by drying to obtain a water dispersible granules.

According to the present invention, it is possible to obtain N-pyridyltoluidine-containing fungicidal water dispersible granules, which are excellently dispersible in water without impairing dispersibility and suspensibility in water and which have a stabilized color as a final product. The N-pyridyltoluidine-containing fungicidal water dispersible granules thus obtained are free from problems such as dusting and disposal of a polluted bottle which used to be inherent to e.g. a wettable powder or a suspension concentrate.

We claim:

1. Fungicidal water dispersible granules, which have a composition consisting essentially of from 20 to 94 wt % of the composition of a fungicide consisting essentially of the fungicidal active component 3-chloro-N-(3-chloro-5-trifluoromethyl-2-pyridyl)-α,α,α-trifluoro-2,6-dinitro-p-toluidine alone or in combination with another fungicidal active ingredient in the ratio of 10 to 70 parts by weight of said fungicidal active component to 10 to 70 parts of weight of the another fungicidal active ingredient, the another fungicidal active ingredient being 1-(2-cyano-2-methoxyiminoacetyl)-3-ethylurea, tetrachioroisophthalonitrile, dimethyl 4,4'-(o-phenylene)bis(3-thioallophanate), 4-[3-(4-chlorophenyl)-3-(3,4-dimethoxyphenyl)acryloyl]morpholine, (RS)-3-(3,5-dichlorophenyl)-5-methyl-5-vinyl-1,3-oxazolidine-2,4-dione, 3-(3,5-dichiorophenyl)-N-isopropyl-2,4-dioxoimidazolidine-1-carboxamide, N-(3,5-dichlorophenyl)-1,2-dimethylcyclopropane-1,2-dicarboximide, 3'-isopropoxy-o-toluanilide, α,α,α-trifluoro-3'-isopropoxy-o-toluanilide, methyl-(E)-methoxyimino [α-(o-tolyloxy)-o-tolyl]acetate, methyl (E)-2-{2-[6-(2-cyanophenoxy)pyrimidin-4-yloxy]phenyl}-3-methoxyacrylate, (E)-2-methoxyimino-N-methyl-2-(2-phenoxyphenyl)acetamide, N-(4,6-dimethylpyrimidine2-yl)aniline or 2-anilino-4-methyl-6-(1-propynyl)pyrimidine, from 2 to 30 wt % of a surfactant, from 1 to 78 wt% of a carrier, from 0 to 3 wt % of an acid as a pH control agent and from 0 to 0.2 wt % of an antifoamer, and the pH of which is adjusted by the surfactant, carrier and/or an acid so that a 1% water suspension thereof will have a pH of from pH 5.0 to 6.8.

2. The fungicidal water dispersible granules according to claim 1, wherein the fungicidal active component is 3-chloro-N-(3-chloro-5-trifluoromethyl-2-pyridyl)-α,α,α-trifluoro-2,6-dinitro-p-toluidine alone.

3. The fungicidal water dispersible granules according to claim 1, wherein the fungicidal active component consists essentially of 3-chloro-N-(3-chloro-5-trifluoromethyl-2-pyridyl)-α,α,α-trifluoro-2,6-dinitro-p-toluidine and the other fungicidal active ingredient in the specified ratios.

4. The fungicidal water dispersible granules according to claim 3, wherein said another fungicidal active ingredient is 1-(2-cyano-2-methoxyiminoacetyl)-3-ethylurea, tetrachloroisophthalonitrile, dimethyl 4,4'-(o-phenylene)bis (3-thioallophanate) or 4-[3-(4-chlorophenyl)-3-(3,4-dimethoxyphenyl)acryloyl]morpholine.

5. The fungicidal water dispersible granules according to claim 1, wherein the fungicidal water dispersible granules are prepared by extruding granulation, spray drying granulation or fluidized bed granulation.

6. A fungicidal water suspension having the fungicidal water dispersible granules as defined in claim 1 suspended in water.

7. The fungicidal water dispersible granules according to claim 1 which contain the acid as a pH control agent.

8. The fungicidal water dispersible granules according to claim 7 wherein the acid pH control agent is citric acid.

9. The fungicidal water dispersible granules according to claim 1 wherein a water-soluble carrier is present in the composition.

10. The fungicidal water dispersible granules according to claim 9 wherein sodium dihydrogen phosphate dihydrate or potassium dihydrogen phosphate is present as a water-soluble carrier.

* * * * *